(12) United States Patent
Pluvinage et al.

(10) Patent No.: US 7,181,297 B1
(45) Date of Patent: Feb. 20, 2007

(54) SYSTEM AND METHOD FOR DELIVERING CUSTOMIZED AUDIO DATA

(75) Inventors: Vincent Pluvinage, Atherton, CA (US); Rodney Perkins, Woodside, CA (US)

(73) Assignee: Sound ID, Palo Alto, CA (US)

( * ) Notice: Subject to any disclaimer, the term of this patent is extended or adjusted under 35 U.S.C. 154(b) by 0 days.

(21) Appl. No.: 09/407,751
(22) Filed: Sep. 28, 1999

(51) Int. Cl.
*G06F 17/00* (2006.01)
*H04R 29/00* (2006.01)
*A61B 5/00* (2006.01)

(52) U.S. Cl. ............................. 700/94; 381/60; 600/559
(58) Field of Classification Search ................. 381/98, 381/100, 102, 104, 105, 57, 315, 320, 60; 340/825.19; 379/52, 346; 600/559; 73/585
See application file for complete search history.

(56) References Cited

U.S. PATENT DOCUMENTS

| | | | |
|---|---|---|---|
| 3,571,529 A | 3/1971 | Gharib et al. ............... | 179/107 |
| 3,718,763 A | 2/1973 | Cannon et al. ................ | 179/1 |
| 3,764,745 A | 10/1973 | Bottcher et al. ............... | 179/1 |
| 3,808,354 A | 4/1974 | Feezor et al. ............... | 179/1 N |
| 3,894,195 A | 7/1975 | Kryter ........................ | 179/107 |
| 3,962,543 A | 6/1976 | Blauert et al. ................. | 179/1 |
| 3,989,904 A | 11/1976 | Rohrer ........................ | 179/107 |

(Continued)

FOREIGN PATENT DOCUMENTS

AU B-52098/96 1/1997

(Continued)

OTHER PUBLICATIONS

Sony Online World—Memory Stick, The Concept, http://www.world.sony.com/Electronics/MS/concept/exp2.html Oct. 11, 1999, pp. 1-3.
Unser "*B-Spline Signal Processing: Part II—Efficient Design and Applications*", IEEE Transactions on Signal Processing, pp. 834-848, vol. 41, No. 2.

(Continued)

*Primary Examiner*—Xu Mei
(74) *Attorney, Agent, or Firm*—Mark Haynes; Haynes Beffel & Wolfeld LLP

(57) ABSTRACT

A method for providing customized audio data products that includes the steps of (1) storing a machine readable hearing profile for a customer, (2) accepting via a data input device or data network for example, machine readable orders from the customer for a particular audio data product, (3) associating the hearing profile for the customer with the particular audio data product, (4) modifying the particular audio data product according to the hearing profile to produce a customized audio data product, (5) delivering the customized audio data product to the customer, for example via a network or by a machine readable storage medium, (6) accepting feedback from the customer concerning the subjective performance of the customized audio data product, and (7) modifying the hearing profile in response to the feedback is provided. A system that includes a source of an audio data product, such as an Internet accessible registry, and processing resources that are configured to receive a request for the audio data product, and to associate the audio data product with a customer hearing profile is provided.

33 Claims, 11 Drawing Sheets

U.S. PATENT DOCUMENTS

| | | | | |
|---|---|---|---|---|
| 4,039,750 | A | 8/1977 | Hull | 179/1 |
| 4,051,331 | A | 9/1977 | Strong et al. | 179/107 |
| 4,201,225 | A | 5/1980 | Bethea et al. | 128/746 |
| 4,284,847 | A | 8/1981 | Besserman | 179/1 |
| 4,289,935 | A | 9/1981 | Zollner et al. | 179/107 |
| 4,425,481 | A | 1/1984 | Mansgold et al. | 179/107 |
| 4,471,171 | A * | 9/1984 | Köpke et al. | 381/60 |
| 4,548,082 | A | 10/1985 | Engebretson et al. | 73/585 |
| 4,622,440 | A | 11/1986 | Slavin | 381/68.1 |
| 4,677,679 | A | 6/1987 | Killion | 381/74 |
| 4,731,850 | A | 3/1988 | Levitt et al. | 381/68.2 |
| 4,791,672 | A | 12/1988 | Nunley et al. | 381/68 |
| 4,868,880 | A | 9/1989 | Bennett et al. | 381/68.2 |
| 4,879,749 | A | 11/1989 | Levitt et al. | 381/68.4 |
| 4,887,299 | A | 12/1989 | Cummins et al. | 381/68.4 |
| 4,926,139 | A | 5/1990 | Anderson et al. | 330/294 |
| 5,027,410 | A | 6/1991 | Williamson et al. | 381/68.4 |
| 5,046,102 | A | 9/1991 | Zwicker et al. | 381/68.2 |
| 5,086,464 | A | 2/1992 | Groppe | 379/430 |
| 5,146,501 | A | 9/1992 | Spector | 381/25 |
| 5,195,132 | A | 3/1993 | Bowker et al. | 379/410 |
| 5,197,332 | A | 3/1993 | Shennib | 73/585 |
| 5,333,195 | A | 7/1994 | Bowker et al. | 379/410 |
| 5,355,418 | A | 10/1994 | Kelsey et al. | 381/72 |
| 5,371,799 | A | 12/1994 | Lowe et al. | 381/25 |
| 5,388,185 | A * | 2/1995 | Terry et al. | 704/205 |
| 5,406,633 | A | 4/1995 | Miller et al. | 381/68.4 |
| 5,406,635 | A | 4/1995 | Jarvinen | 381/94 |
| 5,452,359 | A | 9/1995 | Inanaga et al. | 381/25 |
| 5,485,515 | A | 1/1996 | Allen et al. | 379/391 |
| 5,495,534 | A | 2/1996 | Inanaga et al. | 381/25 |
| 5,500,902 | A | 3/1996 | Stockham et al. | 381/68.4 |
| 5,521,919 | A | 5/1996 | Anderson et al. | 370/68 |
| 5,524,148 | A | 6/1996 | Allen et al. | 379/391 |
| 5,526,423 | A * | 6/1996 | Ohuchi et al. | 379/88.25 |
| 5,539,806 | A | 7/1996 | Allen et al. | 379/52 |
| 5,592,545 | A | 1/1997 | Ho et al. | 379/347 |
| 5,596,507 | A | 1/1997 | Jones et al. | 364/505 |
| 5,608,803 | A | 3/1997 | Magotra et al. | 381/68.2 |
| 5,615,270 | A | 3/1997 | Miller et al. | 381/57 |
| 5,630,159 | A * | 5/1997 | Zancho | 709/221 |
| 5,638,438 | A * | 6/1997 | Keen | 379/354 |
| 5,663,727 | A | 9/1997 | Vokac | 341/132 |
| 5,706,352 | A | 1/1998 | Engebretson et al. | 381/684 |
| 5,717,767 | A | 2/1998 | Inanaga et al. | 381/25 |
| 5,721,783 | A | 2/1998 | Anderson | 381/68.6 |
| 5,737,389 | A | 4/1998 | Allen | 379/1 |
| 5,737,719 | A | 4/1998 | Terry | 704/224 |
| 5,794,201 | A | 8/1998 | Nejime et al. | 704/267 |
| 5,802,164 | A | 9/1998 | Clancy et al. | 379/347 |
| 5,811,681 | A | 9/1998 | Braun et al. | 73/585 |
| 5,848,171 | A | 12/1998 | Stockham et al. | 381/321 |
| 5,854,843 | A | 12/1998 | Jacknin et al. | 381/25 |
| 5,854,978 | A | 12/1998 | Heidari | 455/418 |
| 5,867,457 | A | 2/1999 | Parvulescu et al. | 369/33 |
| 5,868,683 | A | 2/1999 | Protopapas et al. | 600/559 |
| 5,890,124 | A | 3/1999 | Galbi | 704/501 |
| 5,892,836 | A | 4/1999 | Ishige et al. | 381/316 |
| 5,896,449 | A | 4/1999 | Oshidari et al. | 379/347 |
| 5,903,655 | A | 5/1999 | Salmi et al. | 381/321 |
| 5,907,823 | A | 5/1999 | Sjoberg et al. | 704/225 |
| 5,910,990 | A | 6/1999 | Jang | 381/1 |
| 5,923,764 | A | 7/1999 | Shennib | 381/60 |
| 5,928,160 | A | 7/1999 | Clark et al. | 600/559 |
| 5,930,758 | A | 7/1999 | Nishiguchi | 704/500 |
| 5,943,413 | A | 8/1999 | Ash et al. | 379/220 |
| 5,956,674 | A | 9/1999 | Smyth et al. | 704/229 |
| 5,974,380 | A | 10/1999 | Smyth et al. | 704/229 |
| 5,978,762 | A | 11/1999 | Smyth et al. | 704/229 |
| 5,987,418 | A | 11/1999 | Gentit | 704/500 |
| 6,022,315 | A | 2/2000 | Iliff | 600/300 |
| 6,029,126 | A | 2/2000 | Malvar | 704/204 |
| 6,036,496 | A * | 3/2000 | Miller et al. | 434/156 |
| 6,055,502 | A | 4/2000 | Kitamura | 704/500 |
| 6,061,431 | A * | 5/2000 | Knappe et al. | 379/52 |
| 6,072,885 | A | 6/2000 | Stockham et al. | 381/321 |
| 6,078,675 | A | 6/2000 | Bowen-Nielsen et al. | 381/331 |
| 6,094,481 | A | 7/2000 | Deville et al. | 379/390 |
| 6,098,039 | A | 8/2000 | Nishida | 704/229 |
| 6,104,822 | A | 8/2000 | Melanson et al. | 381/320 |
| 6,212,496 | B1 * | 4/2001 | Campbell et al. | 704/221 |
| 6,322,521 | B1 * | 11/2001 | Hou | 600/559 |
| 6,433,801 | B1 * | 8/2002 | Moon et al. | 715/840 |
| 6,463,128 | B1 * | 10/2002 | Elwin | 379/52 |
| 6,674,867 | B2 * | 1/2004 | Basseas | 381/314 |
| 6,684,063 | B2 * | 1/2004 | Berger et al. | 455/90.1 |
| 6,694,143 | B1 * | 2/2004 | Beamish et al. | 455/456.1 |
| 6,913,578 | B2 * | 7/2005 | Hou | 600/559 |
| 2002/0068986 | A1 * | 6/2002 | Mouline | 700/94 |
| 2003/0128859 | A1 * | 7/2003 | Greene et al. | 381/351 |
| 2003/0165247 | A1 * | 9/2003 | Bantz et al. | 381/312 |

FOREIGN PATENT DOCUMENTS

| | | |
|---|---|---|
| DE | 196 00 234 A1 | 7/1997 |
| DE | 299 05 172 U1 | 6/1999 |
| DE | 198 15 373 A1 | 10/1999 |
| EP | 0 329 383 A2 | 8/1989 |
| JP | 11133998 A * | 5/1999 |
| JP | 2000236280 A | 8/2000 |
| WO | WO 95/06996 | 3/1995 |
| WO | WO 98/05150 | 2/1998 |
| WO | WO 98/47314 | 10/1998 |
| WO | WO 98/51124 | 11/1998 |
| WO | WO 98/51126 | 11/1998 |
| WO | WO 99/14986 | 3/1999 |
| WO | WO 99/31937 | 6/1999 |
| WO | WO 00/64350 | 11/2000 |
| WO | WO 01/52737 A1 | 7/2001 |

OTHER PUBLICATIONS

U.S. Appl. No. 60/177,695, filed Jan. 24, 2000 entitled *Remote Hearing Test*, inventor Zezhang Hou.

U.S. Appl. No. 60/189,010, filed Mar. 13, 2000 entitled *Method and System for On-Line Hearing Examination and Correction*, inventor Zezhang Hou.

Braida et al., "*Review of Recent Research on Multiband Amplitude Compression for the Hearing Impaired*" Research Laboratory of Electronics, Massachusetts Institute of Technology Cambridge, Massachusetts pp. 133-140.

Lippmann et al. "*Study of Multichannel Amplitude Compression and Linear Amplification for Persons with Sensorineural Hearing Loss*" Acoustical Society of America February 69(2) 1981, pp. 524-534.

Villchur "*Signal Processing to Improve Speech Intelligibility in Perceptive Deafness*" The Journal of the Acoustical Society of America, vol. 53, No. 6 1973, pp. 1646-1657.

U.S. Appl. No. 09/728,623, filed Dec. 1, 2000 entitled *Adaptation of Audio Data Files Based On Personal Hearing Profiles*, inventor Ali Mouline.

*Wireless Short Message Service (SMS)* TeleCommunication Systems Web ProForum Tutorials pp. 1-18.

Sony Online World—Memory Stick, The Concept, http://www.world.song.com/Electronics/MS/concept/exp2.html (Oct. 11, 1999), pp. 1-3.

* cited by examiner

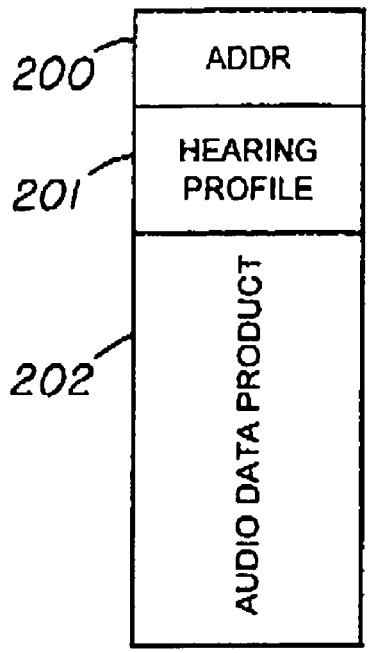
FIG. 4
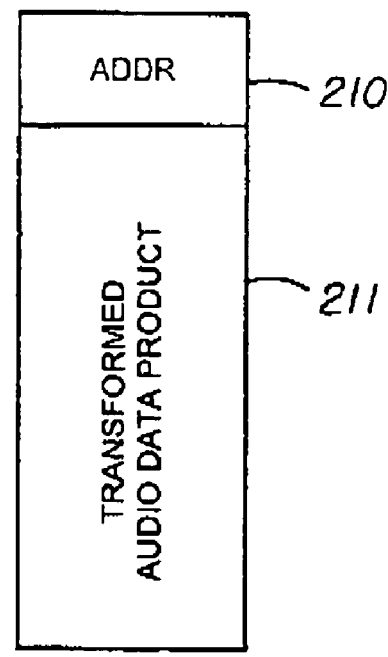
FIG. 5
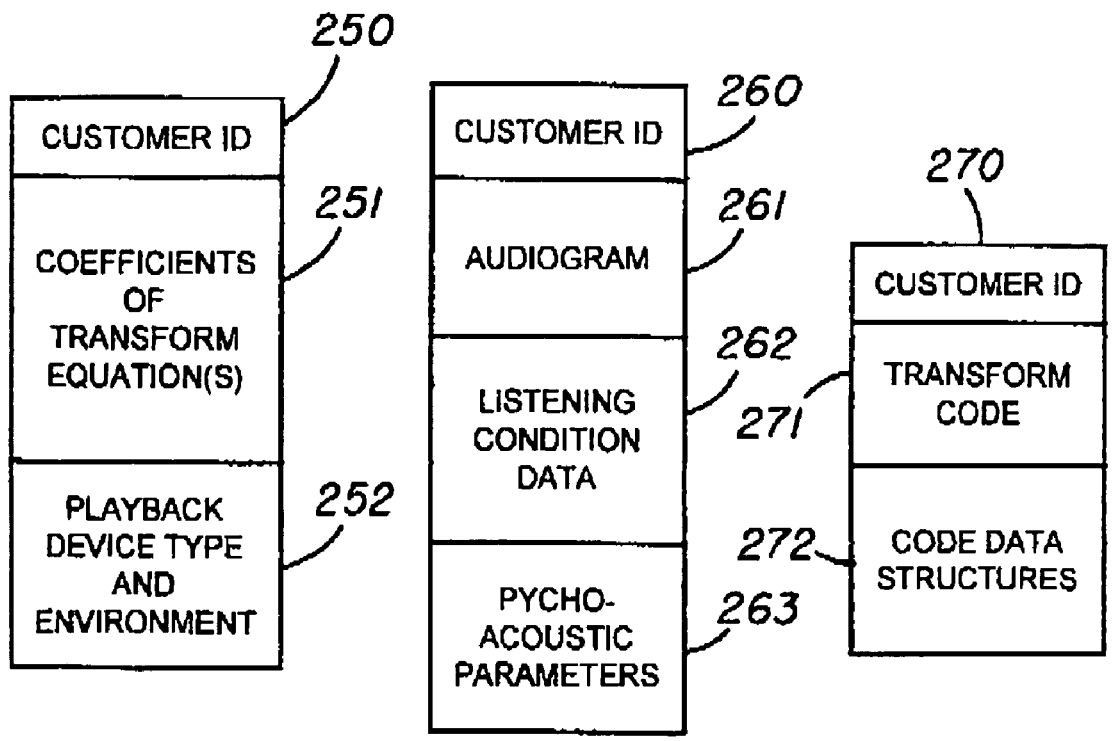
FIG. 6
FIG. 7
FIG. 8

SYSTEM AND METHOD FOR DELIVERING CUSTOMIZED AUDIO DATA

BACKGROUND OF THE INVENTION

1. Field of the Invention

The present invention relates to the distribution and customization of audio data products, like telephone signals, music batch files, and streaming audio data. In particular, the present invention provides for distribution of audio data products customized according to a hearing profile of a customer.

2. Description of Related Art

The hearing profiles of individuals vary in a number of ways. The ability to hear sounds varies with frequency among individuals across the normal audio frequency range. Also, the dynamic range varies among individuals so that levels of audio stimulus that are perceived as soft sounds and levels of audio stimulus that are perceived as loud sounds differ from person to person. Standard hearing tests are designed to produce an audiogram that characterizes such factors as frequency sensitivity and dynamic range in the hearing profiles of individuals. There are also other factors that affect a hearing profile. For example, psycho-acoustic factors concerning the manner in which a person perceives combinations of normal sounds affect the ability to hear in manners that can vary from person to person. Also, environmental factors such as the usual listening environment of a person (library, conference room, concert hall) and the equipment on which the sound is produced (loud speaker, ear phones, telephone hand set), are important. In persons wearing hearing aids or using other assistive hearing devices, the type of aid or device affects the hearing profile. The physiology of an impairment suffered by the individual may also be an important factor in the hearing profile.

Audio products that are distributed to customers in digital or analog electronic form are intended for persons having hearing profiles within a normal range. For example, a popular compression technique for musical compositions being distributed across the Internet, known as MP3, is based on the psycho-acoustic model of a typical listener. Thus, some persons have hearing profiles that may interfere with enjoyment of the MP3 compressed music. Other persons may have hearing profiles which make it difficult to understand normal telephone conversations using audio data from the telephone network. Also, individuals may have hearing profiles which make it impossible to enjoy a musical composition in the way in which it was intended by the composer or musician, even if it were played back with very high fidelity. Other audio data products, such as streaming audio over the Internet, audio accompanying television programs, radio broadcasts, live radio format broadcasts over the Internet, prerecorded audio books and the like, may be difficult for persons having some hearing profiles to fully enjoy.

The hearing profiles of individuals have been applied in the hearing aid field for customizing and fitting hearing aids for individuals. See, for example, U.S. Pat. No. 4,731,850 entitled PROGRAMMABLE DIGITAL HEARING AID SYSTEM, invented by Levitt et al.; and U.S. Pat. No. 5,848,171 entitled HEARING AID DEVICE INCORPORATING SIGNAL PROCESSING TECHNIQUES, invented by Stockham, Jr. et al. Thus, techniques for processing sound to offset variations in hearing are well known. However, these techniques are unavailable to persons not using hearing aids. Furthermore, many persons who could benefit from such processing are not in positions to use hearing aids, for a variety of reasons.

Accordingly, it is desirable to provide systems and methods to apply techniques for the processing of audio data according to hearing profiles for the benefit of individuals who are not wearing hearing assistance devices. Also it is desirable to provide tools to simplify the gathering of information needed to develop hearing profiles of individuals, and to apply the gathered information in the distribution and customization of audio data products.

SUMMARY OF THE INVENTION

The present invention provides customized audio data products, and systems and methods for producing the customized audio data products, for a customer, who may be an individual or a group of individuals, processed according to a hearing profile of the customer. Also, the present invention provides tools for gathering information concerning a customer's hearing profile, and for establishing and optimizing such profile for use in the production of the customized audio data products. According to the present invention, the quality of life as it relates to enjoying music, talking on the telephone, and participating in other listening activities can be improved for a wide range of individuals having hearing profiles that are not typical, whether or not the individual has been fitted with a hearing aid or other assistive hearing device.

In one preferred aspect of the invention, a method executed by a system for providing customized audio data products includes the steps of (1) storing a machine readable hearing profile of a customer, (2) accepting via an input device or data network for example, machine readable orders from the customer for particular a audio data product, (3) associating the hearing profile of the customer with the particular audio data product, (4) modifying the particular audio data product according to the hearing profile to produce a customized audio data product, (5) delivering the customized audio data product to the customer, for example via a network or by a machine readable storage medium, (6) accepting feedback from the customer concerning the objective or subjective performance of the customized audio data product, and (7) modifying the hearing profile in response to the feedback.

In one embodiment of the present invention, the hearing profile and the audio data product are delivered to the customer via separate channels. In one example, the hearing profile is sent via one communication channel to a machine, such as a set top box, at the location in which the audio data product is played, and the audio data product is sent via another communication channel. According to this example, the hearing profile may be provided over the Internet, while the audio data product is provided via a television cable network. In another embodiment, the hearing profile is stored in a portable data storage device, such as a card having a magnetic strip memory, or a card having a non-volatile integrated circuit memory. The hearing profile of the customer in this embodiment is stored on a machine using a portable data storage device. The audio data product is customized by the machine using the hearing profile prior to playback.

The system in various embodiments provides input tools, such as a graphical user interface usable, for example, at a kiosk or accessible via a network, for accepting input data concerning a hearing profile of a customer. The input tools are used for creating a machine readable hearing profile, which is stored in a registry of hearing profiles for use in the production of customized audio data products. Alternatively, the hearing profile is stored on a portable data storage medium for use by the customer, as described above.

Also, in various embodiments of the invention, the system provides tools for accepting input data characterizing the feedback from the customer. Processing resources are provided for modifying the machine readable hearing profile in response to the feedback data. The modifying of the machine readable hearing profile in one aspect of the invention comprises applying an optimization modeling process to the hearing profile, by which the profiles are improved over time using feedback arising from a variety of customized audio data products and from a variety of listening conditions.

According to other aspects of the invention, the system includes resources for determining a type of delivery for the customized audio data product, such as by prompting a customer to select a delivery mode. The step of modifying the particular audio data product is responsive to the type of delivery requested by the customer. Thus, for example, if a customer requests a music batch file to be delivered using the MP3 compression technique, the processing algorithm applied, or the parameters applied in a single algorithm, may be different than that applied if the customer requests a telephone conversation delivered via a telephone network customized according to the customer's hearing profile.

The present invention also provides a system that includes a source of an encoded audio data product, and processing resources that are configured to receive a request for the encoded audio data product, and to associate the encoded audio data product with a customer hearing profile. The customer hearing profile is used for production of a customized audio data product.

The customer hearing profile comprises in various embodiments, the coefficients of the transfer function used to transform an audio data product according to a hearing characteristic of a customer, and an identifier of a transfer function used to transform the encoded audio data product, an identifier of a transfer function and coefficients for the identified transfer function, values indicating listening conditions in which the customized audio data product is to be played, specification of psycho-acoustic characteristics of a customer, an audiogram characterizing physical hearing characteristics of a customer, and executable software defining a transfer function for producing the customized audio data product. Thus it can be seen that the hearing profile used for production of the customized audio data product according to the present invention assumes a structure adapted to the distribution of processing and communication resources in the particular system being utilized.

The data processing resources are adapted according to the network resources available. Thus, the processing power for transforming the selected audio data product into the customized audio data product can be positioned at a central location accessible via a network, it can be distributed at a variety of locations in the network, it can be positioned in the playback device at a customer's home or office, and it can be implemented using combinations of processors located in several sites.

The architecture of the system can assume a variety of configurations. In one aspect, the processing resources in the system include a network interface and logic to accept via the network interface data concerning the customer for use in producing the customer's hearing profile. In other embodiments, the system includes a source of a plurality of customer hearing profiles, such as a customer registry. In response to a request for a particular audio data product, the hearing profile is retrieved from the registry and used for production of the customized audio data product.

A variety of user interface tools, such as Web pages, other tools accessible via a network, graphical user interfaces executed on a customer terminal, graphical user interfaces executed at a terminal in a kiosk, personal digital assistant (PDA) devices with network interfaces, and telephones, are included in various embodiments of the invention for accepting data concerning hearing profiles, selections of audio data products, selections of delivery modes, and other input data utilized in the system.

The resources used for associating a customer hearing profile with an audio data product are centrally located at a site accessible via a network by a large customer base. However, in various embodiments, these resources can be distributed among a variety of sites accessible via a network. In a similar manner, the database for storing the hearing profiles of customers is coupled with the site used for associating the hearing profile with an encoded audio data product. Alternatively, the database is distributed among a variety of locations for the purposes, for example, of load balancing, security and redundancy.

The customized audio data product is likewise implemented according to the particular configuration of the network processing and communication resources. Thus, the customized audio data product in various embodiments consists of the hearing profile, or portions of the hearing profile, concatenated with the selected audio data product for processing, or further processing, after delivery. In other embodiments, the customized audio data product includes the encoded audio data product transformed using the hearing profile, and ready for play back, prior to delivery.

The encoded audio data product, which is customized and delivered according to the present invention comprises in various embodiments analog or digital instances of pre-recorded audio tracks, pre-recorded audio music tracks, live audio music streams, pre-recorded audio voice tracks, live audio voice tracks, live audio telephone data, audio tracks associated with television programs or movies, or other kinds of batch or streaming mode audio data.

The present invention also supports a variety of modes of delivery for the customized audio data product. The customized audio data product is delivered in various embodiments by providing resources to store the customized audio data product on machine readable storage media, such as CD ROM, DVD, or other storage media formats suitable for shipping to the customer. In one preferred embodiment, the customized audio data product is transmitted via a network to the customer using a format such as MP3, formats for voice over the Internet VoIP, or standard telephone formats. The network in various embodiments includes the Internet, a private network, a telephone network, a satellite communications network, or other wired or wireless communication technologies. The transmitted customized audio data product is adapted for a particular playback device in one embodiment. Thus, the product is adapted for transmission to a personal computer, to a hand-held PDA having a wireless communication link, or directly to a playback device with a wired or wireless network interface.

Thus, the present invention provides a comprehensive system and method for providing audio data products customized according to individual hearing profiles of customers. The system and method operate without requiring assistance of specialized listening devices or hearing aids and allow for optimization of the hearing profiles and customizing processes according to characteristics of the customer, to the particular audio data product being customized, and the listening environment in which the product is to be enjoyed. Utilizing the techniques of the present invention, greater numbers of people may take advantage of the processing techniques developed in the hearing aid arts to account for variations in hearing profiles of individuals. Further, the need for hearing aids or other assistive listening devices will be reduced, and many people will be able to avoid the need for such devices completely.

Other aspects and advantages of the present invention can be seen on review of the drawings, the detailed description, and the claims which follow.

BRIEF DESCRIPTION OF THE FIGURES

FIG. 4 is a diagram of one example of a customized audio data product according to the present invention.

FIG. 5 is a diagram of another example of a customized audio data product according to the present invention.

FIG. 6 is a diagram of one example of a hearing profile for use in producing customized audio data products.

FIG. 7 is a diagram of another example of a hearing profile for use in producing customized audio data products.

FIG. 8 is a diagram of yet another example of a hearing profile for use in producing customized audio data products.

DETAILED DESCRIPTION

A detailed description of the various embodiments of the present invention is provided with reference to FIGS. 1 through 20.

Figure 1:
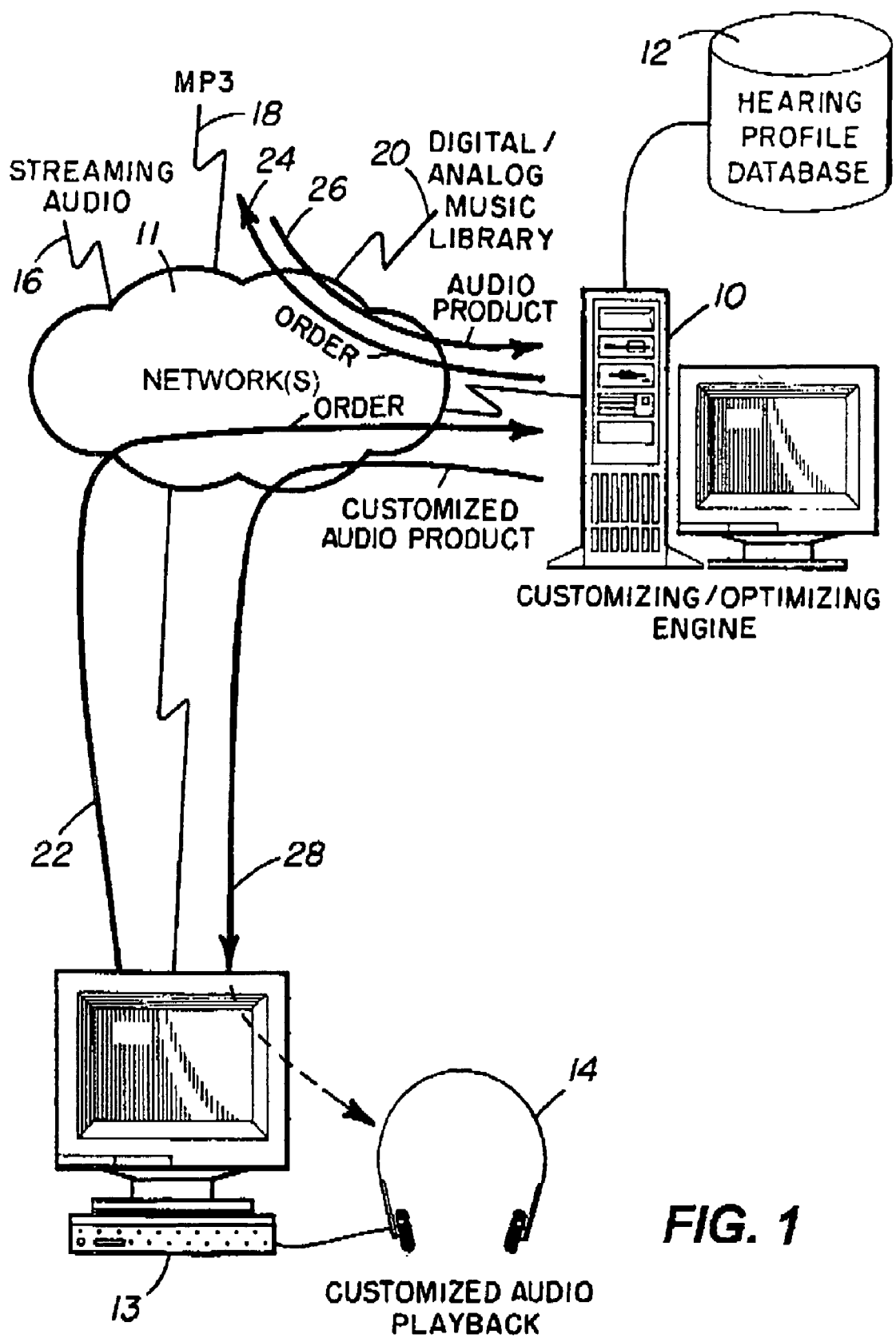
FIG. 1 is a diagram of one example system for delivering customized audio data products according to the present invention.

FIG. 1 provides an illustration of one example system for delivering customized audio data products. Other examples will be discussed below. The system includes a server 10 which is coupled to a network or networks 11 for communication with other network connected devices. The server 10 is also coupled to a database 12 storing hearing profiles of customers. In this example, a customer has a personal computer 13 which is coupled to the network or networks 11. The personal computer 13 includes data processing resources, such as memory, a graphical user interface program, and a digital signal processing based sound board coupled with ear phones 14 for playing back an audio product stored in the PC or being received via the network through the PC. The network or networks 11 interconnect services to supply audio data products. In this example, suppliers of streaming audio are represented by the line 16, suppliers of MP3 batch files are represented by the line 18, and suppliers of digital and analog music library files are represented by the line 20.

In this example, the server 10 includes a variety of data processing resources, including a network interface or interfaces, a host processor for managing an Internet based service, memory resources, and a processor, such as a digital signal processor, used in the customizing of audio data products, and used for optimizing hearing profiles stored in the database 12. In this example, the network interface or interfaces of the server 10 act as a source of audio data products. The user issues an order via the network as represented by line 22, for a particular audio data product. Resources in the server 10 translate the order into a form, as represented by line 24, for retrieving the audio data product from the network. The particular audio data product requested by the customer is returned via the network as represented by line 26 to the server 10. Data processing resources in the server 10 associate a hearing profile from the hearing profile database 12 with the particular audio data product. The customized audio data product is then returned as represented by line 28 via the network to the customer PC 13. The PC 13 processes the customized audio data product and supplies it for customized audio playback at the ear phones 14.

The system of FIG. 1 also provides data processing resources for gathering information needed for developing and storing hearing profiles in the database 12. In addition, the system includes resources for obtaining feedback from customers used in the optimizing of hearing profiles.

Figure 2:
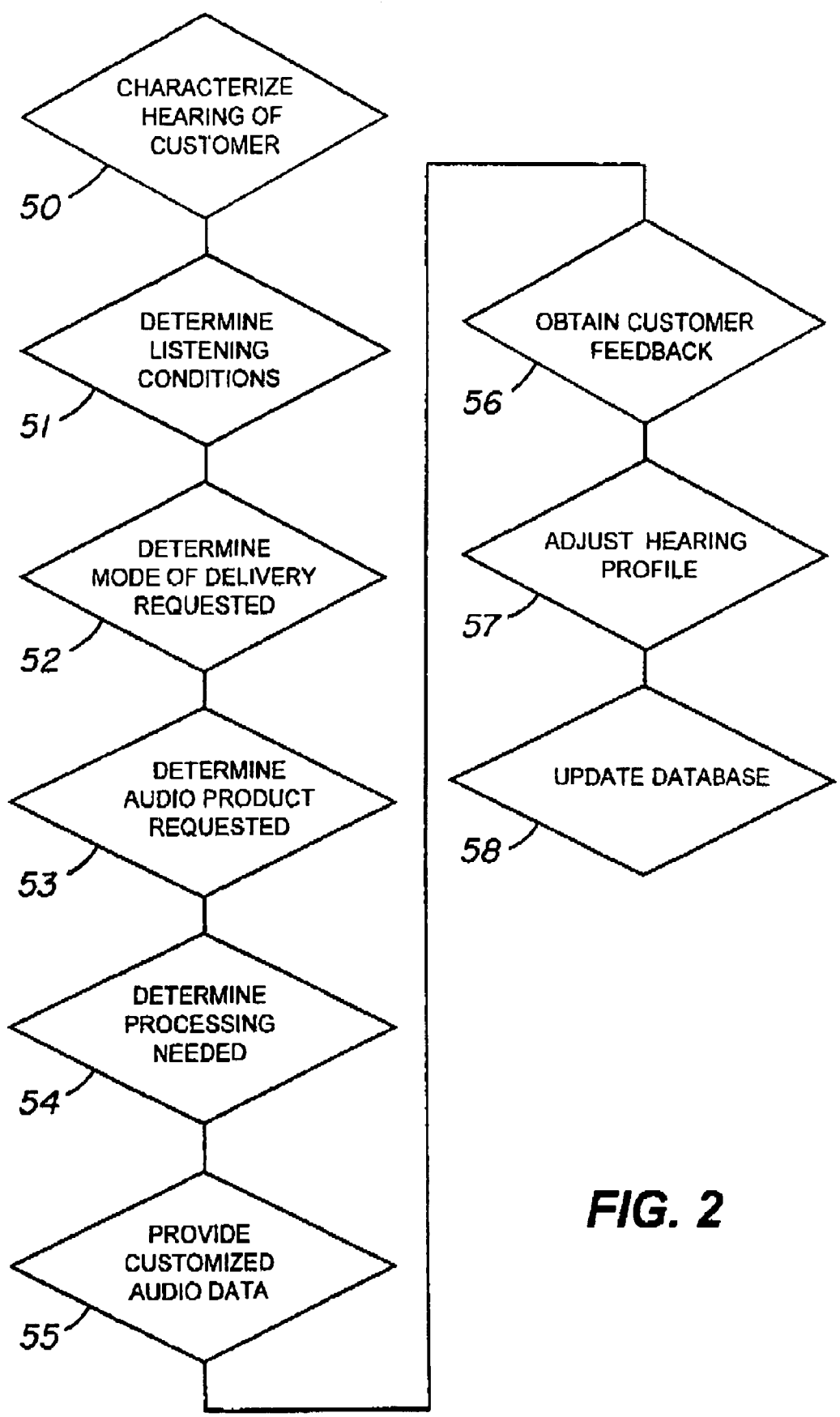
FIG. 2 illustrates a method for delivering customized audio data products according to the present invention.

FIG. 2 illustrates a basic method of operation of a system according to the present invention. Although FIG. 2 is drawn in the form of a flow chart, the particular sequence of steps can be modified as suits particular implementation or context of execution.

A first step in the method is to characterize the hearing of a customer (block 50). The hearing of a customer can be characterized in the system of the present invention indirectly, such as by entering an audiogram, entering the make of the hearing aid and assorted prescription, if any is used by the customer, or entering responses to questionnaires. This indirect input data is processed by the system to produce a hearing profile which can be used in a production of customized audio data products. Alternatively, the hearing of a customer may be characterized directly. For example, a customer may sample a closed set of hearing profile choices and select a preferred one. Alternatively, a network based test can be executed by which information needed for administering the test is delivered to the customer via the Internet or other network, and the customer's responses to stimulus in the test are returned via the network to the processing resources in the system. In another example, a kiosk is set up in a public location for use by customers to establish a hearing profile using the processing resources of the kiosk designed for administering the hearing tests. In yet another embodiment, a test is administered over the telephone, particularly when the audio data product to be delivered is telephone calls. These direct measurements of the hearing profile of the customer are processed by the system into hearing profiles used for customizing audio data.

Another process in the method of the present invention is to determine the listening conditions in which the customer will be using the customized audio data product (block 51). The listening conditions may include free field environments in which the transducers consist of loud speakers in a living room being driven by a television, radio, or a home stereo, speakers in an automobile driven by the automobile sound system, or concert conditions of some sort. Other listening conditions may be monaural, such as a telephone or an existing prosthetic device. In another example, listening conditions consist of binaural settings, in which sounds are to be delivered via a headset or a binaural prosthetic device. The listening conditions can be characterized in the hearing profile to be applied for producing the customized audio data product.

The next process illustrated in FIG. 2 in the method of the present invention involves determining the mode of delivery of the audio data product which the customer has requested (block 52). The audio data product after it has been customized, can be delivered on a storage medium, or via a network. Also, the format of delivery, such as an MP3 batch file to be played after it has been delivered and stored on the customer's machine, or a streaming audio product which can be listened to while it is being downloaded from the Internet from a live source or from a stored library of audio products, may be subject to different customization algorithms.

The system also includes resources for determining the audio product requested by the customer (block 53). These resources may be implemented using well-known Internet server techniques for commercial transactions and for presenting catalogs of goods or services. Examples of audio products which may be requested include pre-recorded music, live music performances, radio broadcasts, radio format streaming audio products, telephone calls, television shows, audio books and any other audio data source.

Based upon one or more of the processes in blocks 50–53, the system determines the processing needed to customize the audio data product (block 54). The information gathered in the processes of blocks 50–53 are applied using the principles developed for customizing and fitting hearing aids, and improved using adaptive optimization processes as discussed below.

The processing is applied, and the customized audio data is provided to the customer according to the mode of delivery requested (block 55). The customized audio data may take on a variety of formats as discussed in more detail below.

Another process provided by the system is to obtain customer feedback concerning the objective and subjective performance of the customized audio data (block 56). The feedback is retrieved using Internet based techniques for gathering data in one embodiment. Alternatively, customers can be called on the telephone or prompted to fill out questionnaires to rate the performance of the products.

Utilizing the feedback obtained, the hearing profiles are adjusted (block 57). Adjustments may be made either on the fly, or offline as is determined by the processing resources available, and the type of product being delivered. For example, for streaming audio products it may be desirable to optimize the customization of the product on the fly so that the customer can experience the improvements resulting from feedback being returned to the system within a short period of time.

The final process illustrated in the method of FIG. 2 is to update the database used for storing hearing profiles based upon the adjustments made in response to customer feedback (block 58). In this manner, a database is developed of hearing profiles, including the adjustments made to hearing profiles based on specific kinds of feedback for specific kinds of audio data products. Using information in the database, the system is able to improve techniques for establishing and adjusting hearing profiles over time according to adaptive optimization techniques. In addition, the database may be used as a resource for delivering other products to the customer.

Figure 3:
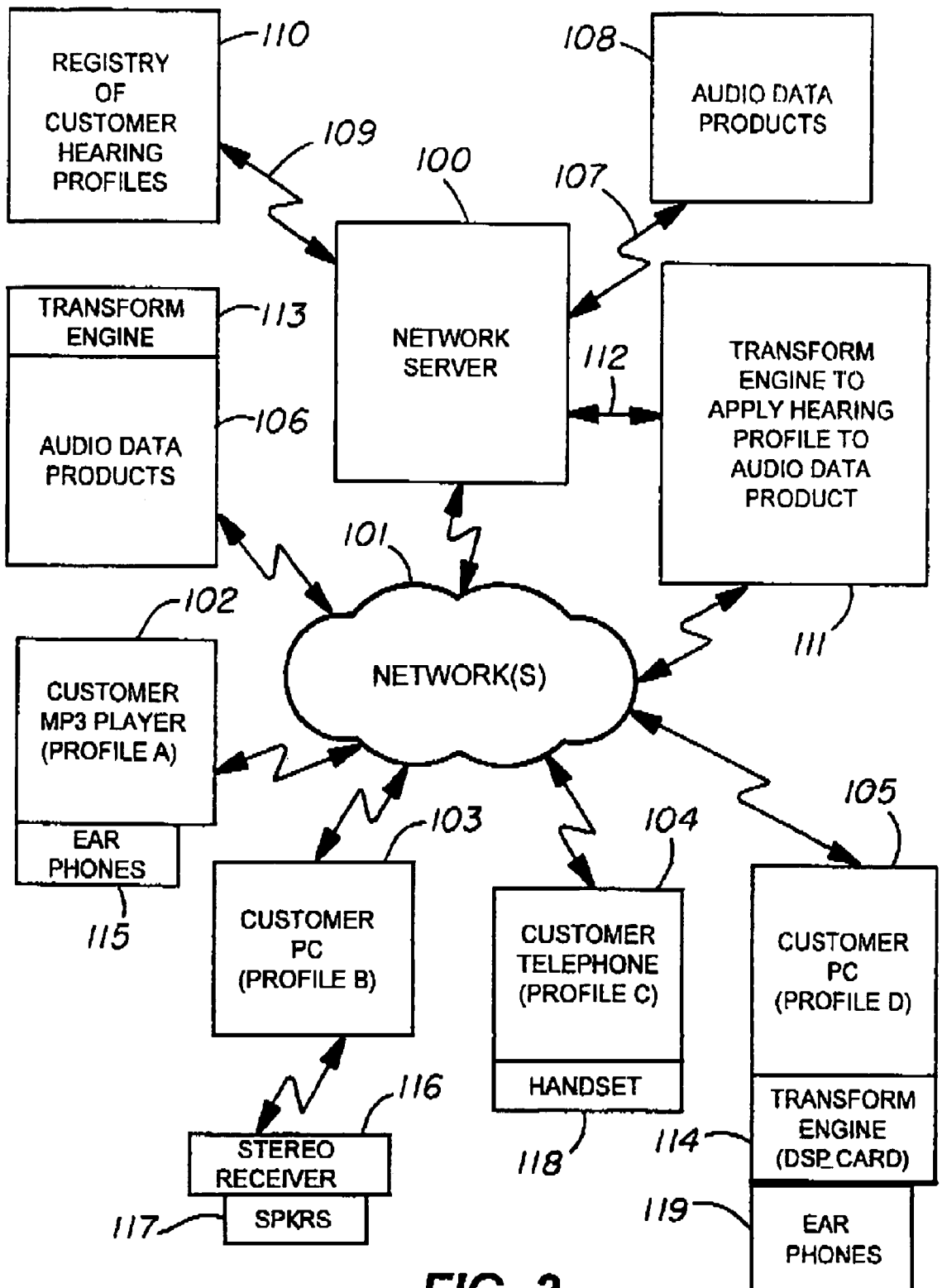
FIG. 3 is a heuristic diagram illustrating a variety of system configurations and implementations of the present invention.

FIG. 3 is a diagram used for illustrating a variety of configurations of the system of the present invention. It will be apparent to persons of skill in the art that a large number of variations in architecture for a network based data processing system can be applied, depending on such issues as load balancing, security, reliability, and speed.

FIG. 3 illustrates a system that includes a network server 100 which is coupled to a network or networks 101. A plurality of customer and stations, including customer end station 102, customer end station 103, customer end station 104, and customer end station 105 are coupled to the network 101. Also, the network interconnects suppliers of audio data products, such as audio data product server 106. The network server 100 also includes a separate link 107 to another supplier of audio data products 108. Also, connected to the server 100 via a link 109 is a registry of customer hearing profiles 110, such as a database which stores hearing profiles accessible using customer identifiers. In this example, a transform engine 111 is coupled to the network server 100 via link 112, and also to the network 101. The transform engine 111 includes the resources for applying hearing profiles to an audio data product, in order to produce the customized audio data products for delivery to the customer. The configuration of FIG. 3 also includes other transform engines distributed in the system. Thus, the server 106 for delivering audio data products includes a transform engine 113. Also, the customer end station 105 consists of a personal computer including a transform engine 114 based on, for example, a digital signal processing card.

The customers end station 102–105 illustrate a variety of playback modes which may be served by the system of the present invention. Thus, the customer end station 102 consists of an MP3 player, which transduces batch mode MP3 music files for supply to ear phones 115. The customer end station 103 consists of a personal computer which is coupled to a stereo receiver 116 which drives loud speakers 117. Customer end station 104 consists of a telephone which supplies the customized audio data to a telephone handset 118. Customer end station 105 consists of personal computers with an on-board transform engine which supplies the audio data transformed to match the hearing profile of the customer to ear phones 119.

The network 101 is illustrated in FIG. 3 as a single entity. However, the network may comprise a plurality of networks, including the telephone network, the World Wide Web, private networks, land based wireless networks, satellite communication networks, and other forms of data communication. The plurality of networks by which audio data products may be communicated can be used alone, or in combination as suits the particular communication channel being set up to deliver the product.

In one preferred mode, the particular audio data product selected by the customer has a particular format, such as an MP3 format. The customized audio data product is also delivered in the particular format of the original audio data product. In this manner, the customer is able to playback the customized audio data product using the type of equipment for which the original product was developed. In alternative embodiments, the customized audio data product is transformed from the format of the original audio data product into the format of the listening device in which the customer intends to play back the customized audio data product.

The server 100 in one preferred embodiment includes resources for keeping information used for billing the customer for ordering customized audio data products.

FIGS. 4 and 5 illustrate alternative formats for the customized audio data product according to the present invention. In FIG. 4, the customized audio data product consists of a header 200 that includes, for example, a destination address, a field 201 holding the hearing profile, or portions of the hearing profile, and a field 202 holding the audio data product which has been retrieved and modified by the addition of the header 200 and hearing profile 201. The format of the customized audio data product shown in FIG. 4 is utilized when the transform engine is located at the customer site or remote from the server at which the hearing profile is associated with the audio data product to be delivered.

FIG. 5 illustrates an alternative format for a customized audio data product which includes a header 210, including a destination address, and a field 211 holding a transformed version of the audio data product. The format of the customized audio data product shown in FIG. 5 is utilized when the transform engine is coupled with the network server which associates the hearing profile with the particular audio data product to be delivered.

FIGS. 6, 7 and 8 illustrate alternative formats for the hearing profiles to be stored in the registry 110. The hearing profile shown in FIG. 6 includes a customer ID 250, coefficients of transform equations 251, and an identifier of the playback device type and listening environment 252 in which the audio data product is to be played. In FIG. 7, the hearing profile includes a customer identifier 260, the audiogram for customer 261, listening condition data 262, and psycho-acoustic parameters 263 which relate to the listening characteristics of the customer. The hearing profile shown in FIG. 8 includes a customer identifier 270, and software 271 along with code data structures 272 that in combination provide executable transform code for producing the customized audio data product from the selected audio data product. The three examples of hearing profile formats shown in FIGS. 6–8 are representative of a large number of hearing profile formats that could be utilized depending on the type of transform processes being executed, the type of audio products being delivered, and other factors related to the architecture of the system.

Figure 9:
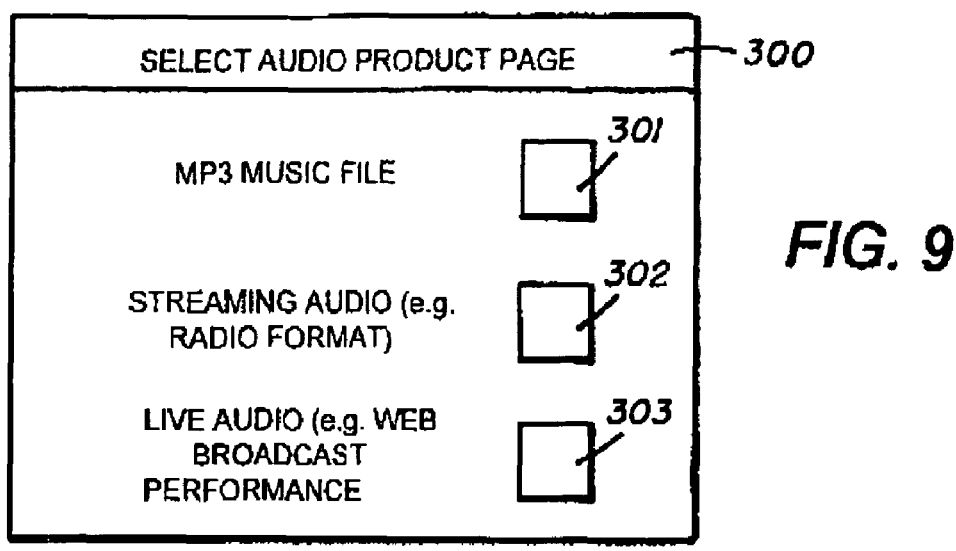
FIG. 9 is a simplified diagram of a user interface for selecting a particular audio product in conjunction with the system of the present invention.
Figure 10:
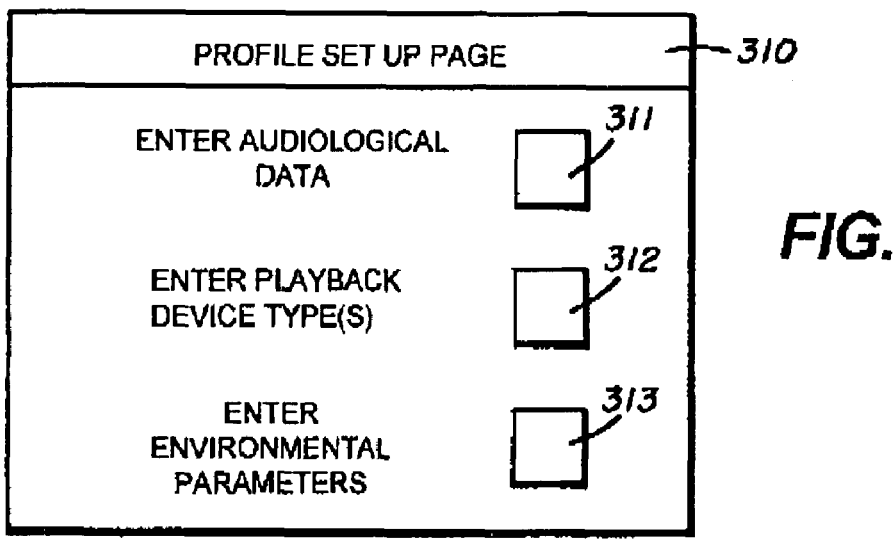
FIG. 10 is a simplified diagram of a user interface for setting up a hearing profile for a customer in conjunction with the system of the present invention.
Figure 11:
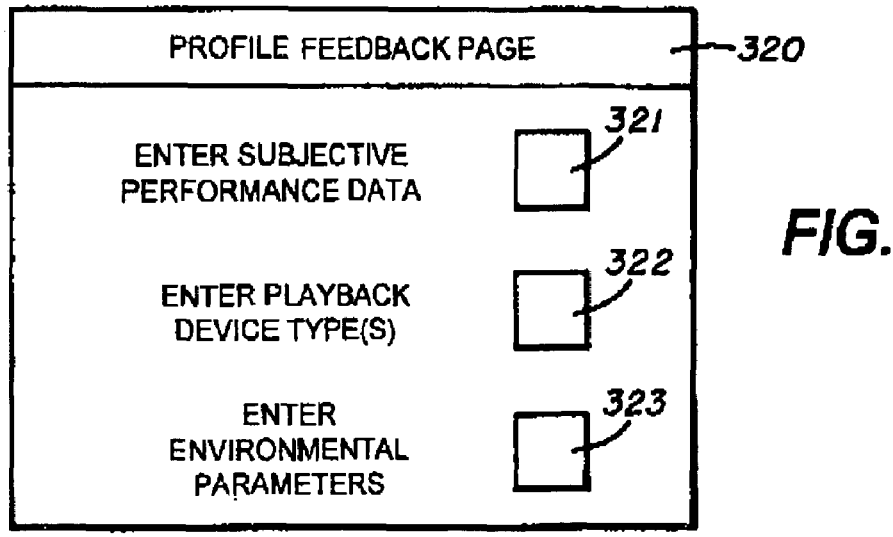
FIG. 11 is a simplified diagram of the user interface for obtaining feedback from a customer concerning a hearing profile in conjunction with the present invention.

As mentioned before, the system of the present invention provides user input tools for selecting audio products, for setting up hearing profiles, and for providing feedback about the performance of the customer's audio data products. FIGS. 9 through 11 show simplified graphic user interface pages used for prompting a user to input data for these purposes. Thus, FIG. 9 shows a page 300 prompting the user to select an audio product. The page 300 includes a first graphical tool 301 for selecting an MP3 music file; a second graphical tool 302 used for selecting streaming audio such as a radio format data, and a third tool 303 used for selecting live audio products, such as a web broadcast performance, or telephone call. FIG. 10 shows a simplified user interface page 310 for setting up a hearing profile. In this example, the page 310 includes a tool 311 for entering audiological data, such as an audiogram. The tool 312 is provided for allowing a user to enter playback device types. The tool 313 is included on the page 310, prompting the user to enter environmental parameters. FIG. 11 shows a simplified user interface page 320 prompting the user to provide feedback concerning the hearing profile. Thus in this example, the tool 321 is provided prompting the user to enter subjective performance data, such as whether the customized audio data products sounded good or bad, or whether the pitch of the product was too high or too low. Also, tool 322 is provided to allow the user to update the playback device types being used. Finally, in the example of FIG. 11, the tool 323 is provided by which the user is prompted to update parameters about the environment. The pages shown in FIGS. 9–11 are obviously simplified versions showing a range of possibilities for input tools provided by the system of the present invention.

Figure 12:
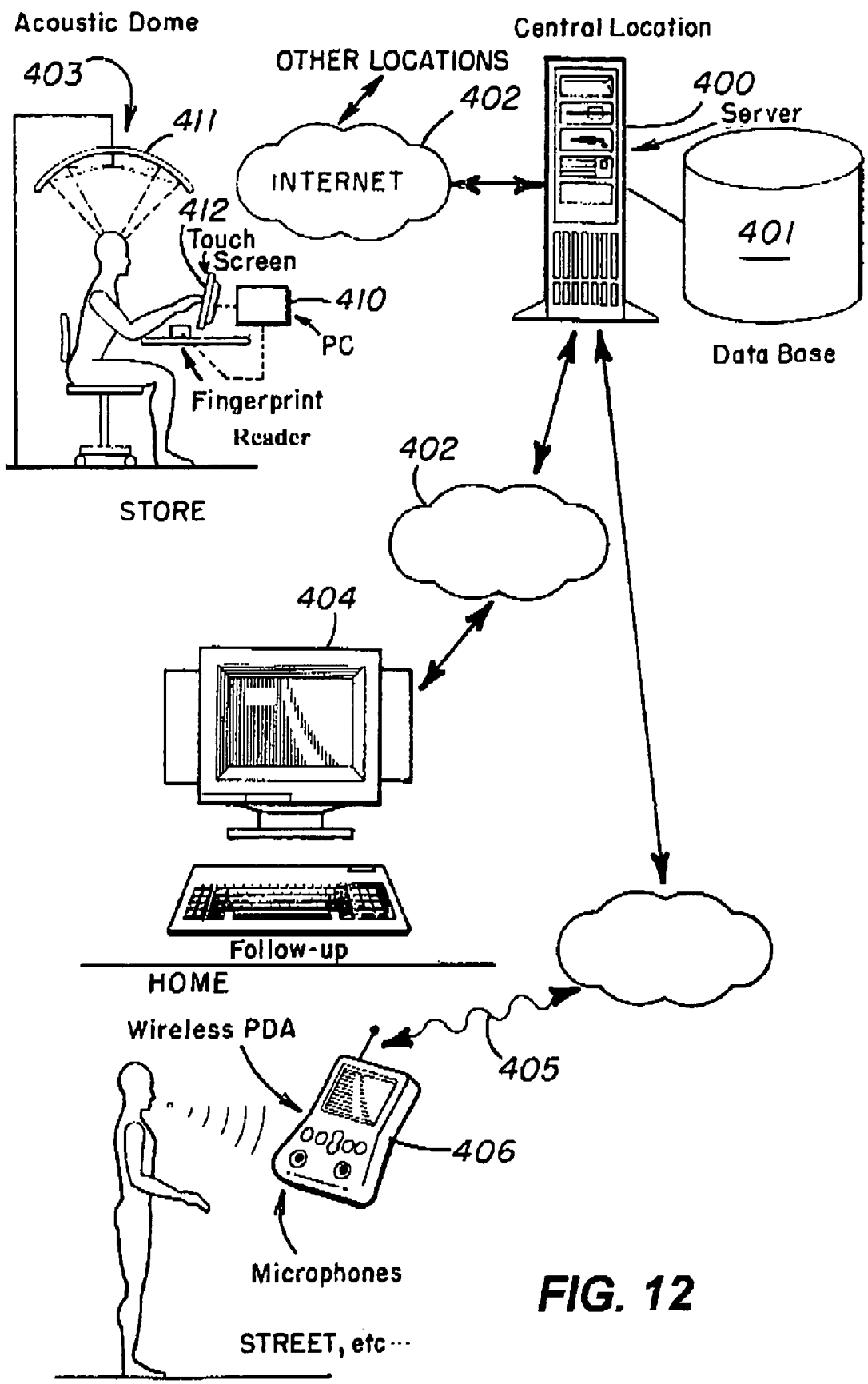
FIG. 12 illustrates environments in which input data is received from customers in conjunction with the production and optimization of hearing profiles according to the present invention.

FIG. 12 illustrates a variety of scenarios by which a central server 400 interacts with customers in the development and optimization of hearing profiles, and for the selection and delivery of customized audio data products. Thus, the system in FIG. 12 consists of the server 400 which is coupled to the database 401 storing hearing profiles. The server 400 is coupled to the Internet 402, and via Internet 402 to a kiosk 403, and to a plurality of other locations, including a personal computer 403 at the home of the customer, and via wireless link 405 to a personal digital assistant 406, by which the customer provides feedback away from home. The kiosk 403 includes a computer 410 having a graphical user interface such as a touch screen 411 for administering a hearing test to gather data for development of hearing profiles. In the preferred embodiment, sounds used in the test are provided using an acoustic dome 411, such as the stereo sound dome unit known as a Virtual Audio Imager provided by Brown Innovations, Inc. of Chicago, Ill. Utilizing the acoustic dome 411, carefully controlled audio vectors are generated and directed to the customer for use in direct measurement of the customer's hearing profile. A sequence of graphic user interface screens are presented on the touch screen 412, in combination with the audio stimulus provided by the acoustic dome 411. The user's hearing profile is developed based on interaction via the touch screen 412.

The personal computer 404 at the customer's home is utilized for follow-up interaction with the customer, or for gathering indirect data concerning the hearing profile of the customer. Thus, via the Internet 402, the server 400 can deliver questionnaires and simple audio tests to the home PC 404. Also, a user can access a web page, or use electronic mail, to provide feedback concerning the performance of the customized audio data product that had been played by the user. Finally as shown in FIG. 12, the user may access the server 400 using a wireless personal digital assistant 406 to provide feedback concerning the performance of the customized audio data product.

Figure 13:
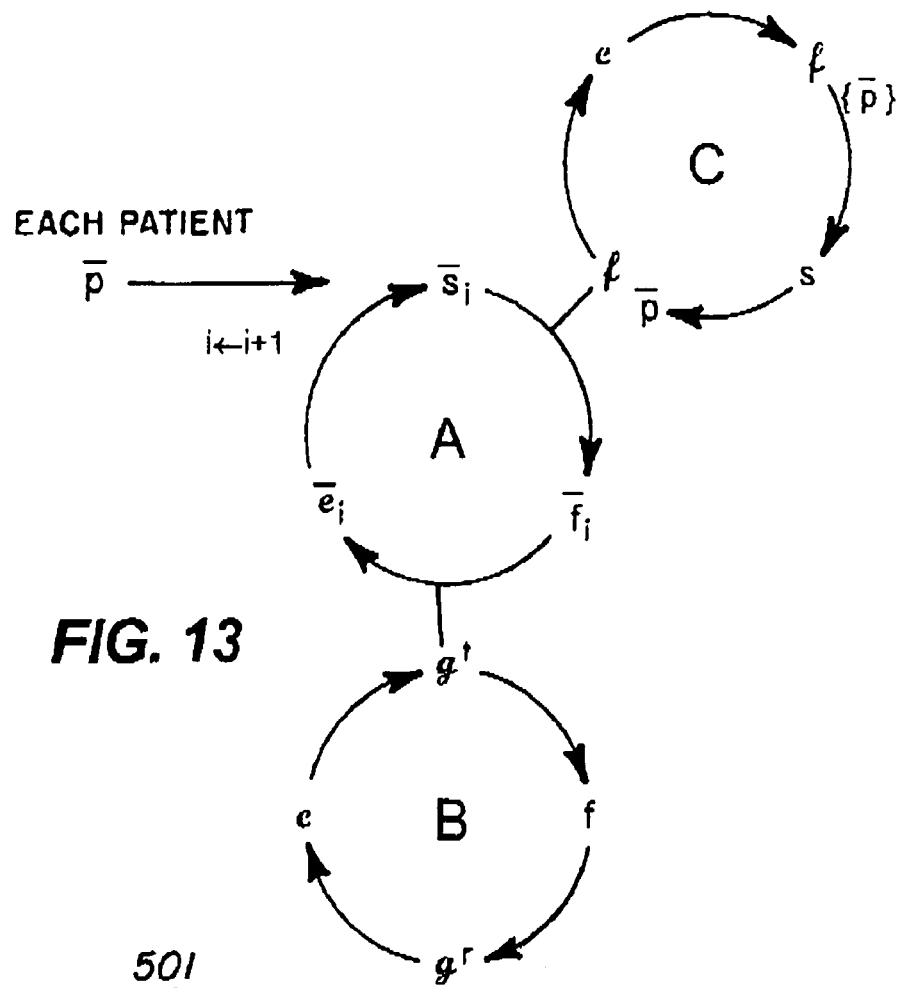
FIG. 13 illustrates optimization loops, and the interaction among optimization loops for producing hearing profiles according to the present invention.

FIG. 13 illustrates optimization loops used for the production of a customer's hearing profile according to the present invention. The first optimization loop A is based on administration of an interative test. For each customer, the vector "s" representing a sound environment, a vector "f" representing a fitting parameter, and a vector "e" representing the customer's evaluation at this stage of the test is developed. The sequence of stimuli is applied to produce the vectors. The vectors are applied to a second loop C. In the second loop C, a fitting algorithm is executed based upon the aggregate of data from many patients. In this loop, data mining techniques can be used to make a best initial guess of the fitting to be applied to the customer. The fitting being developed for the customer is applied to a feedback loop B. In the feedback loop B, the fitting "f" developed during the test for the profile represented by transform $g^t$ is applied to a real world environment $g^r$. The evaluation "e" provided by the customer in response to the real world experience is used in feedback for the purposes of optimization of the fitting.

Figure 14:
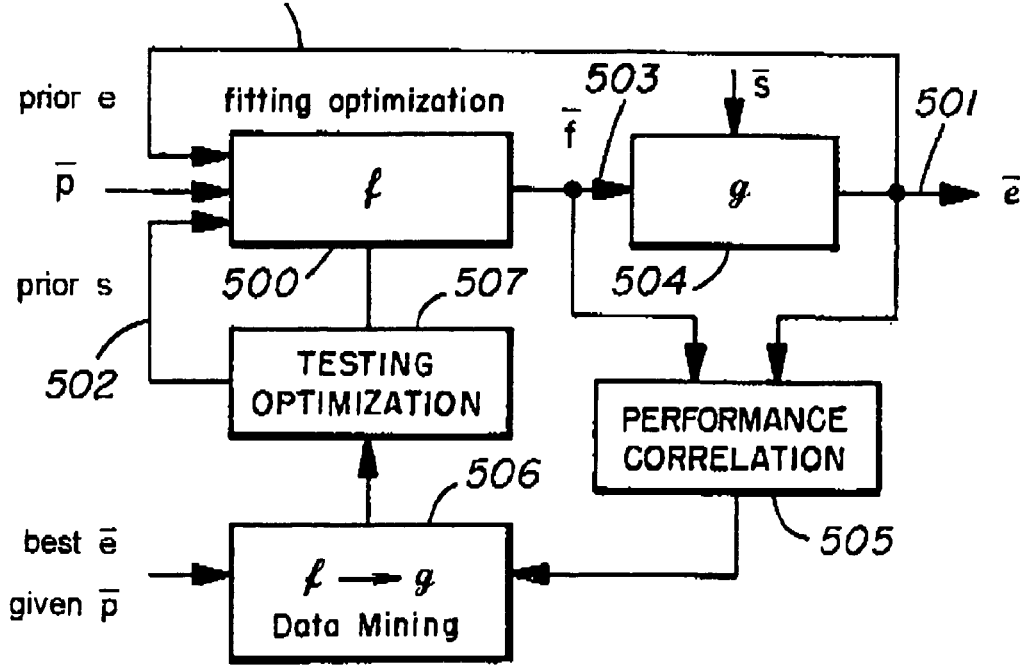
FIG. 14 illustrates processing resources for dynamic optimization of hearing profiles according to the present invention utilizing reference model adaptive control techniques.

FIG. 14 illustrates processing resources used in the adaptive optimization of a hearing profile according to the present mention invention. The customer's profile "p" is applied to a fitting processor 500. Other inputs to the fitting processor 500 include prior evaluation data provided on line 501, prior sound environment data delivered online 502, and customer input. A particular fitting vector "f" is provided on line 503. This fitting vector is processed according to a transfer function 504. Customer evaluation of the playback is provided on line 501. The fitting vector on line 503 and the evaluation on line 501 are fed to a performance correlation unit 505. The performance correlation unit 505 generates a result that is applied to data mining resources 506 for the purposes of determining a reaction to the correlation result. Data mining produces parameters used in testing optimization unit 507. A testing optimization unit 507 updates the environmental parameters for the customer. The data mining resources 506 are seeded with the information gathered from prior evaluations for given customers. Thus, model reference adaptive learning using data mining techniques can be utilized to optimize the fitting for a particular customer. For additional information concerning model reference adaptive optimization techniques, reference can be made to LANDAU, *ADAPTIVE CONTROL, THE MODEL REFERENCE APPROACH*, Merkel Dekker, Inc. New York, 1979.

Figure 15:
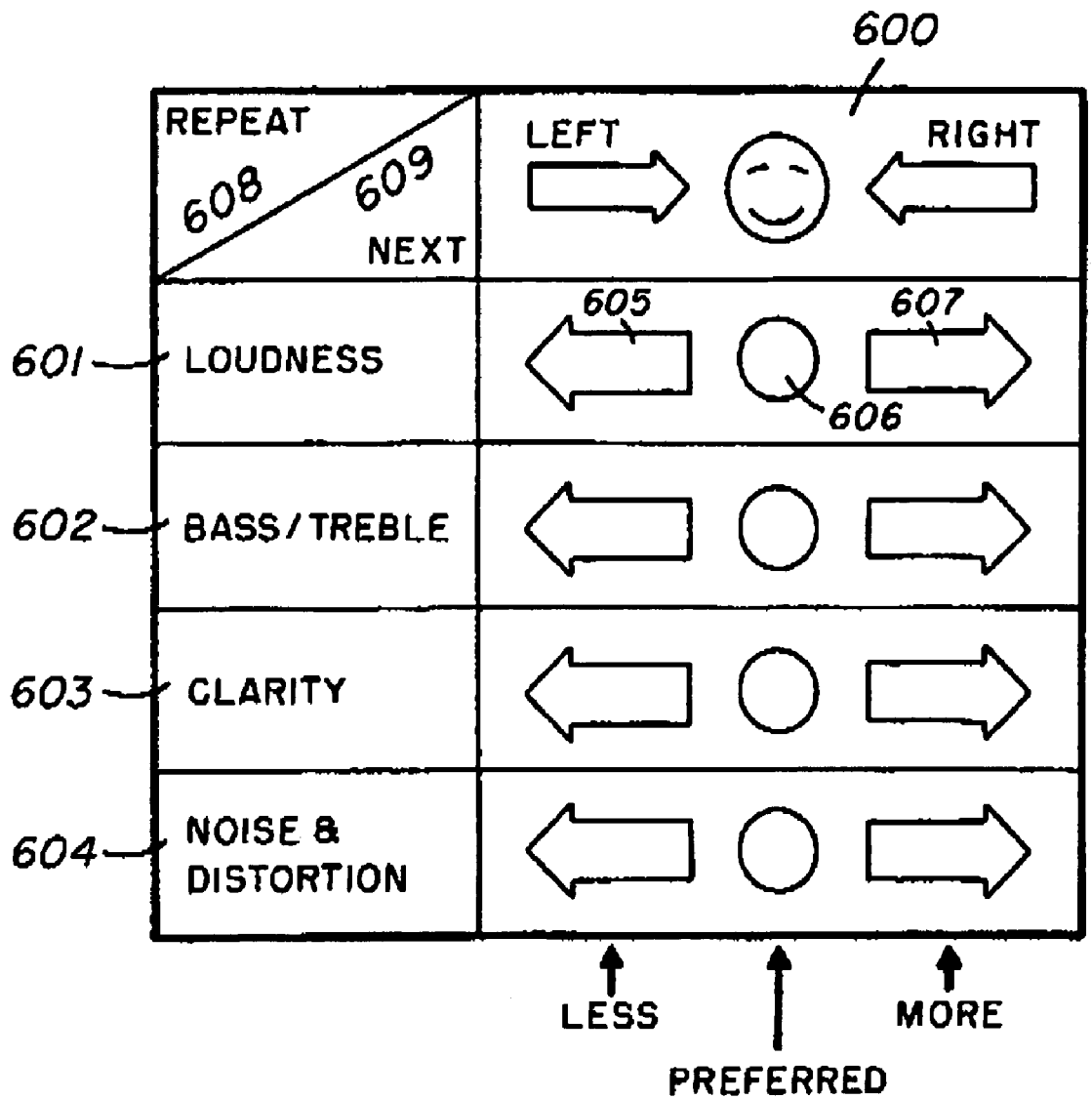
FIG. 15 illustrates a graphical user input tool for the purposes of gathering information concerning a hearing profile of a customer.

FIGS. 15–18 illustrate graphical user interface tools for use in a kiosk environment such as the kiosk 403 shown in FIG. 12, for development of a hearing profile using direct measurements. The user interface of FIG. 15 provides a simple interface for gathering information about the profile of the user. The tool includes a first indicator 600 for signaling to a user whether the left or right ear is being stimulated. Next, a label using either text or graphics is displayed for indicating to the user that a test for loudness is being made. Next, a label 602 for bass and treble tests is provided. A label 603 for testing clarity is provided. A label 604 is provided identifying tests for noise and distortion. The user is given the option of making three selections for each test represented by a left facing arrow 605, a center button 606, and a right facing arrow 607. Thus, for example during a loudness test for the left ear, an indicator in region 600 identifies stimulus to the left ear. A sound is played using the acoustic dome 411 shown in FIG. 12. The user selects the left arrow if the tone is too loud, the right arrow if the tone is too soft, and the center button 606 if the tone sounds right.

Similar stimulus-response tests are administered for the other factors to be determined. The upper left-hand section of the screen includes a button 608 to signal to repeat the test, and a button 609 to signal that the user is ready to proceed to a next test. Using this stimulus-response technique, with limited feedback options, a basic hearing profile can be developed without professional assistance.

Figure 16:
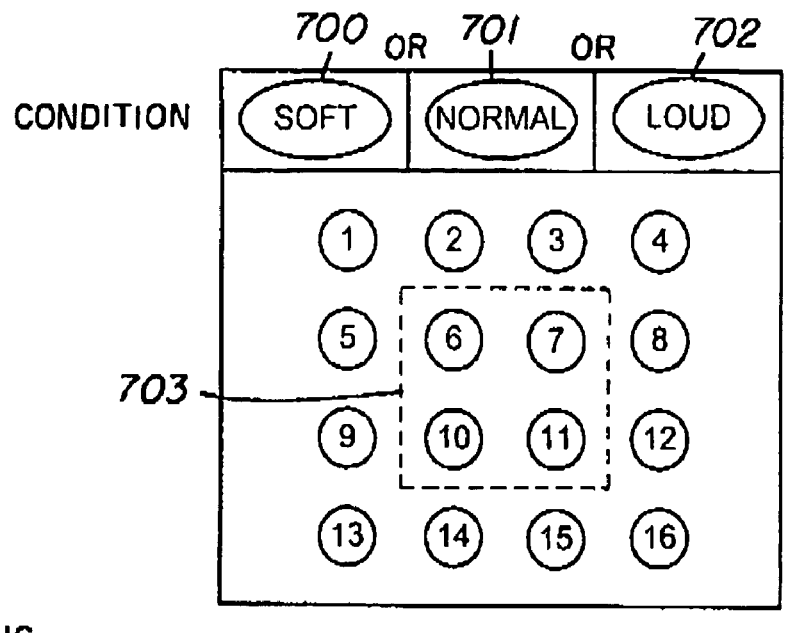
FIG. 16 illustrates another graphical user input tool for gathering information concerning hearing profiles of customers.
Figure 17:
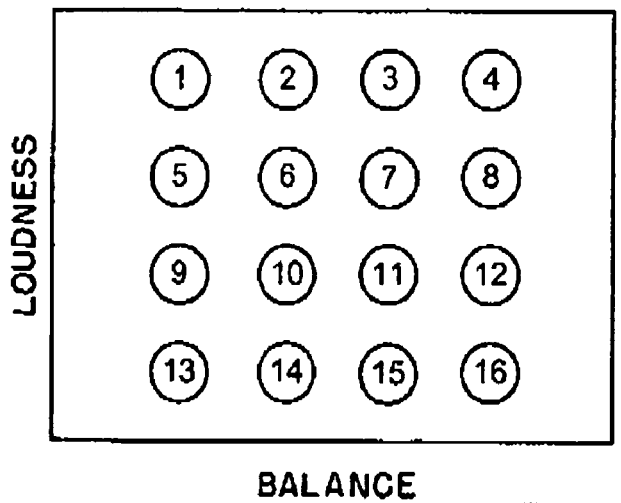
FIG. 17 illustrates a second level graphical user input tool used in conjunction with the input tool of FIG. 16.
Figure 18:
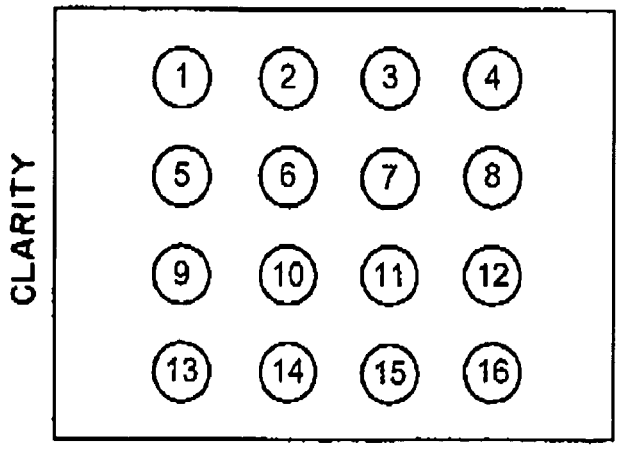
FIG. 18 illustrates another second level graphical user input tool used in conjunction with the input tool of FIG. 16.

FIGS. 16–18 illustrate another technique for gathering feedback from a customer during the development of a hearing profile. A first screen as shown in FIG. 16 is displayed with a row of condition indicators 700–702 across the top of the screen. The indicators show whether the test being executed is adapted to determine soft sounds, normal sounds, or loud sounds. An array of 16 buttons arrayed in a 4 by 4 matrix in this example is displayed to the user. A set of sound stimulus is played, the user is instructed to select a corresponding button in the 16 button array. After a first selection, preferably within the interior four buttons in the region 703 of the array, a second screen, such as the screen shown in FIG. 17 is displayed to the customer, linked to the choice made in the first screen. The second screen (FIG. 17) includes a second array of 16 buttons presented to the user. The user again selects a preferred setting for a loudness over balance of the stimulus to further refine the profile data. FIG. 18 illustrates another second level screen for the purposes of selecting the preferred level of clarity over noise and distortion for the signal. Utilizing these graphical interface tools in combination with audio stimulus, relatively sophisticated information concerning users' hearing profiles can be gathered automatically by an Internet based, or kiosk based, testing system.

Figure 19:
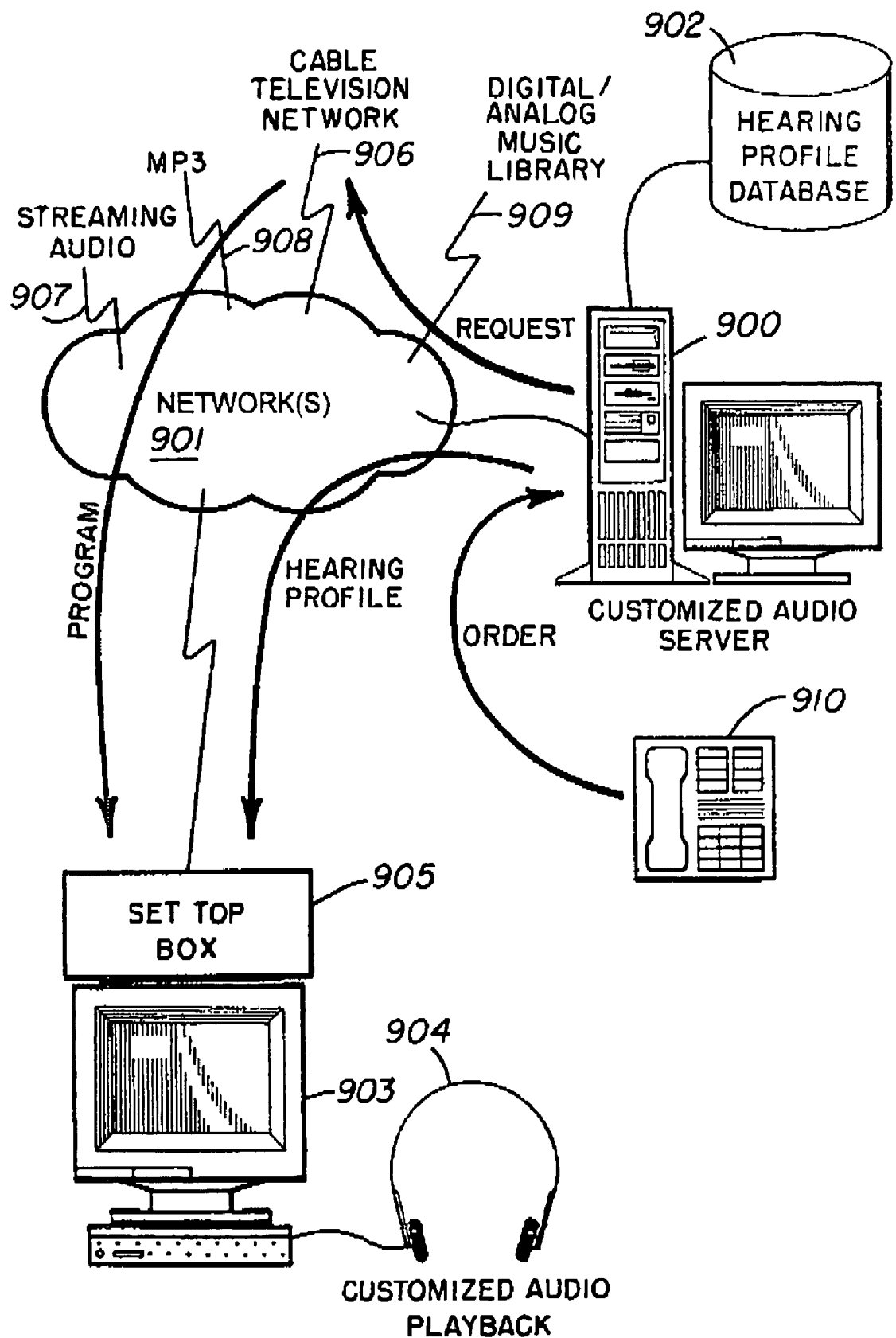
FIG. 19 illustrates a configuration of an alternative system according to the present invention in which the hearing profile is applied in a set top box, and delivered via a communication channel different than that used for the audio data product.

FIG. 19 illustrates another system configuration for the delivery of customized audio data products according to the present invention. The system includes a customized audio server 900 which is coupled to a network or networks 901 for communication with other network connected devices. The servers are also coupled to a hearing profile database 902, such as described above. In this example, a customer has a display system 903 which may be a computer monitor, a television, or another device that is coupled to the network or networks 901. The display system 903 is coupled to an audio system for providing playback of the customized audio, in this example using headphones 904. Also coupled to the display system is a set top box 905 by which the display system is coupled to the network or networks 901. The set top box 905 combines the hearing profile data and the program including audio data to produce the customized audio data product at the customer site.

In one example, the set top box is coupled to a cable television network 906 across which movies and television programming that include audio data products are supplied to the display system 903. Thus, one source of audio data products coupled to the network or networks 901 is cable television network 906. Other sources of audio data products coupled to the network or networks 901 include streaming audio data 907, MP3 encoded audio data 908, and a digital/analog music library 909.

The customized audio server 900 acts as a gateway for managing the delivery of customized audio data products. In this example, the customized audio server 900 is also coupled to the telephone network, as indicated by the telephone 910. One example transaction using the system of FIG. 19 includes placement of an order for customized audio data products using the telephone 910 using touch tone commands or voice recognition mechanisms. When the order is placed to the customized audio server 900, a request is issued to the source of the requested audio data product, in this example to the cable television network, for delivery of a chosen audio data product. Also, the customized audio server 900 transmits a hearing profile to the set top box 905 across a communication channel between the customized audio server 900 and the set top box 905. The cable television network 906 transmits the requested programming including the audio data product to the set top box 905 using a separate communication channel. Thus, for example, the hearing profile is transmitted from the customized audio server 900 to the set top box 905 using the Internet, while the programming is supplied from the cable television network 906 using the television cable protocols and media. Also, separate Internet channels may be used for the independent channels from the customized audio server 900 and from the source of the audio data.

In other transactions using the system of FIG. 19, the order may be placed via the communication link between the set-top box 905 and customized audio server 900, or via other communication links with the customized audio server 900. Also, feedback concerning the performance of the customized audio data product can be provided using the set top box 905 or via other communication channels to the customized audio server 900. In other configurations, the database 902 is coupled to the network or networks 901 at a site apart from the customized audio server 900.

Figure 20:
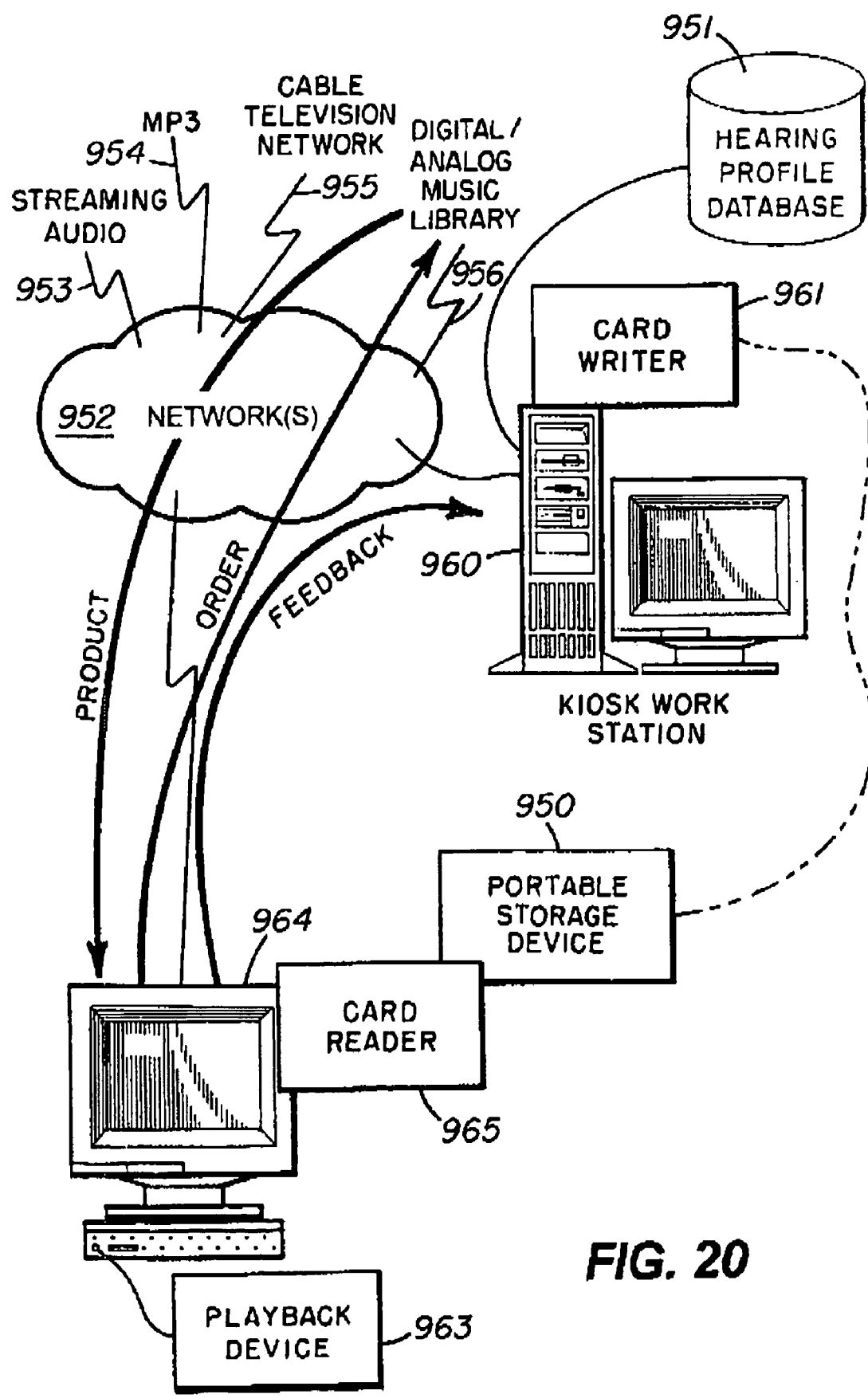
FIG. 20 illustrates a configuration of an alternative system according to the present invention in which the hearing profile is provided using a portable storage device for use by a customer to produce customized audio data.

FIG. 20 illustrates another system configuration for producing customized audio data products according to the present invention in which the hearing profile is carried on a portable storage device 950, such as a plastic card having a magnetic strip or carrying an integrated circuit memory. In this example, a hearing profile database 951 is coupled to the network or networks 952. A plurality of sources of audio data products are also coupled to the network or networks 952, including, for example, streaming audio data 953, MP3 encoded audio data 954, cable television network 955, and a digital/analog music library 956. In the system shown in FIG. 20, a kiosk workstation 960 is coupled to the network or networks 952. Using the workstation 960 and the tools described above for the creation of a hearing profile, an individual generates a hearing profile data set. A card writer 961, or other resource for storing data on a portable storage device 950 is coupled to the kiosk workstation 960. The hearing profile data is stored on the portable storage device 950 and the individual carries it to a location at which a playback device 963 is used to play the customized audio. The user has a personal computer 964, or other network connected appliance, which is coupled to the network or networks 952. Coupled with personal computer 964 is a card reader 965 by which the data in the portable storage device 950 is downloaded to the personal computer 964.

A transaction using the system of FIG. 20 includes a user issuing an order for a particular customized audio data product directly to the source of the product. Thus, in this example, the order for a customized audio data product is placed directly to the digital/analog music library 956. The selected audio data product is delivered to the personal computer 964. The personal computer 964 uses the hearing profile from the portable storage device 950 to produce the customized audio data product, and delivers it to the playback device 963. In one embodiment, the personal computer 964 is also configured to provide feedback information concerning the performance of the customized audio data product. The feedback information is delivered via the network or networks 952 to the hearing profile database server 951.

Portable storage devices carrying hearing profile data may be used in a variety of settings. For example, a card reader may be coupled to a set top box for a cable or satellite television network to allow for the delivery of customized audio data with standard programming. Also, a card reader and headphone set may be installed in a movie theater to allow for the delivery of customized audio data to moviegoers. Card readers may be coupled to telephones to allow for the correction of audio telephone conversations. Examples of portable storage devices include plastic cards with magnetic strips, PC Card format or PCMCIA format add-on cards for computers, flash memory cards, cards like the "Memory Stick" provided by Sony Corporation, a floppy disk, or other machine readable storage devices adapted to be carried from machine to machine.

Also, in various embodiments of the present invention, customer identification data, such as fingerprints or other biometric data, may be recorded and stored with the hearing profile of a customer for purposes of authentication of feedback data, automatic accounting for use of the hearing profile data, and other purposes.

In summary, the present invention provides a system and method for producing hearing profiles for customers to be used in the production of customized audio data products. The hearing profiles allow for the customized and optimized sound processing for each customer. The process can be optimized over time and over situations and for each modality for the delivery of the sound product. The customized audio data products are delivered via a variety of communication channels, to specific playback devices or to generic playback devices as suits a particular customer.

The system and method of the present invention provide for delivery of optimized audio products to persons that do not use hearing aids or other assistive hearing devices. Audio products from a variety of sound data sources can be customized using hearing profiles, and delivered to a customer on demand.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the appended claims.

What is claimed is:

1. A method for producing customized audio data, comprising:
   executing an interface at a server or network of servers in a data network for selection of audio data products from, and for access to, a catalog of audio data products;
   providing a graphical user interface to a customer at a customer terminal, the graphical user interface presenting the catalog of audio data products from which a customer is able to select an audio data product;
   receiving, at the server or network of servers, a request for a particular audio data product from the catalog of audio data products wherein the request is made by the customer via the graphical user interface;
   receiving, at the server or network of servers, a customer hearing profile associated with the customer from a machine readable registry of customer hearing profiles, the customer hearing profile comprising data adapted to be applied to transform the particular audio data product according to hearing a characteristic of the customer to produce a customized audio data product;
   obtaining, at the server or network of servers, the particular audio data product; and associating, at the server or network of servers, the particular audio data product with the customer hearing profile producing said customized audio data product in response to the particular audio data product and the associated customer hearing profile, and delivering the customized audio data product to the customer terminal for use by the customer.

2. The method of claim 1, wherein the customer hearing profile comprises coefficients of a transfer function to transform the audio data product according a psycho-acoustic characteristic of a customer.

3. The method of claim 1, wherein the customer hearing profile comprises an identifier of transfer function to transform the audio data product according a hearing characteristic of a customer.

4. The method of claim 1, wherein the customer hearing profile comprises an identifier of a transfer function and coefficients of the identified transfer function to transform the audio data product according a hearing characteristic of a customer.

5. The method of claim 1, wherein the machine readable registry comprises customer hearing profiles corresponding to registered customers, and further including reading, modifying and writing particular customer hearing profiles in the plurality to maintain the registry.

6. The method of claim 1, wherein the catalog of audio data products comprise pre-recorded audio tracks.

7. The method of claim 1, wherein the catalog of audio data products comprise pre-recorded audio music tracks.

8. The method of claim 1, wherein the catalog of audio data products comprise live audio music streams.

9. The method of claim 1, wherein the catalog of audio data products comprise pre-recorded audio voice tracks.

10. The method of claim 1, wherein the catalog of audio data products comprise live audio voice streams.

11. The method of claim 1, wherein the catalog of audio data products comprise live audio telephone data.

12. The method of claim 1, wherein the graphical user interface includes tools by which a user selects an instance of the audio data product, and issues a request for the selected instance.

13. The method of claim 1, including providing tools by which a user adds a customer hearing profile to the registry.

14. The method of claim 1, including providing tools by which a user modifies a particular customer hearing profile in the registry.

15. The method of claim 1, including providing logic to produce information about billing for requested audio data products for customers.

16. The method of claim 1, wherein the catalog of audio data products comprises a digitally encoded product.

17. The method of claim 1, wherein the catalog of audio data products comprises an analog encoded product.

18. The method of claim 1, wherein the catalog of audio data products comprises data encoded according to a particular format suitable for playback by audio devices adapted for the particular format, and the customized audio data product comprises data encoded according to the particular format.

19. The method of claim 1, wherein a customer hearing profile in the registry includes a value indicating an audio device on which the customized audio data product is to be played.

20. The method of claim 1, wherein the customer hearing profile includes a value indicating a hearing characteristic type of a customer for whom the customized audio data product is to be played.

21. The method of claim 1, wherein the customer hearing profile includes a specification of psycho-acoustic characteristics of a customer for whom the customized audio data product is to be played.

22. The method of claim 1, wherein the customer hearing profile includes an audiogram of a customer for whom the customized audio data product is to be played.

23. The method of claim 1, wherein the customer hearing profile includes software defining a transfer function for producing the customized audio data product.

24. The method of claim 1, including accepting data concerning a customer for whom the customized audio data product is to be played, and producing a customer hearing profile for registry in response to the accepted data.

25. The method of claim 1, including accepting data via a network interface concerning a customer for whom the customized audio data product is to be played, and producing a customer hearing profile for the registry in response to the accepted data.

26. The method of claim 1, including accepting data via a network interface concerning a customer for whom the customized audio data product is to be played, and modifying a customer hearing profile in the registry in response to the accepted data.

27. The method of claim 1, including providing a source of a plurality of customer profiles, providing an interface accessible to a user via a network interface to accept data concerning a customer for whom the customized audio data product is to be played, and producing a customer profile for the registry in response to the accepted data.

28. The method of claim 1, including providing an interface accessible to a user via a network interface to accept data concerning a customer for whom the customized audio data product is to be played, and modifying a customer hearing profile in registry in response to the accepted data.

29. The method of claim 1, wherein the catalog of audio data products includes a plurality of variant types of audio data products.

30. The method of claim 1, wherein the customized audio data product comprises a data structure including selected audio data product unmodified and data representing the customer hearing profile, wherein the data structure is adapted for processing at the customer terminal to produce a modified audio signal.

31. A method for producing customized audio data, comprising:
executing an interface at a server or network of servers in a data network for selection of audio data products from, and for access to, a catalog of audio data products;
providing a graphical user interface to a customer at a customer terminal, the graphical user interface presenting the catalog of audio data products from which a customer is able to select an audio data product;
receiving, at the server or network of servers, a request for a particular audio data product from the catalog of audio data products wherein the request is made by the customer via the graphical user interface;
receiving, at the server or network of servers, a customer hearing profile associated with the customer from a machine readable registry of customer hearing profiles, the customer hearing profile comprising data adapted to be applied to transform the particular audio data product according to hearing a characteristic of the customer to produce a customized audio data product;
obtaining, at the server or network of servers, the particular audio data product;

associating, at the server or network of servers, the particular audio data product with the customer hearing profile producing said customized audio data product in response to the particular audio data product and the associated customer hearing profile; and storing the customized audio data product on a portable machine readable medium.

32. The method of claim 31, wherein the catalog of audio data products includes a plurality of variant types of audio data products.

33. The method of claim 31, wherein the customized audio data product comprises a data structure including selected audio data product unmodified and data representing the customer hearing profile, wherein the data structure is adapted for processing at the customer terminal to produce a modified audio signal.

\* \* \* \* \*